United States Patent
Phillips (10) Patent No.: US 7,140,592 B2
(45) Date of Patent: Nov. 28, 2006

(54) SELF-SEALING MALE LUER CONNECTOR WITH BIASED VALVE PLUG

(75) Inventor: John C. Phillips, New Hill, NC (US)

(73) Assignee: Cardinal Health 303, Inc., San Diego, CA (US)

( * ) Notice: Subject to any disclaimer, the term of this patent is extended or adjusted under 35 U.S.C. 154(b) by 101 days.

(21) Appl. No.: 10/335,242

(22) Filed: Dec. 31, 2002

(65) Prior Publication Data

US 2004/0124389 A1    Jul. 1, 2004

(51) Int. Cl.
*F16K 31/50* (2006.01)

(52) U.S. Cl. ............... 251/149.6; 251/149.1; 251/340; 604/249; 604/905

(58) Field of Classification Search ............. 251/149.1, 251/149.4, 149.6, 149.7, 149.8, 149.9, 320, 251/321, 322, 323, 340, 339, 341, 347, 348; 604/246, 249, 905
See application file for complete search history.

(56) References Cited

U.S. PATENT DOCUMENTS

| | | | | |
|---|---|---|---|---|
| 2,061,012 A | * | 11/1936 | Wade | 251/149.5 |
| 2,506,722 A | * | 5/1950 | Kuehn et al. | 251/322 |
| 2,591,514 A | * | 4/1952 | Courtot | 251/323 |
| 2,842,382 A | * | 7/1958 | Franck | 251/149.4 |
| 4,430,073 A | * | 2/1984 | Bemis et al. | 604/249 |
| 4,522,592 A | * | 6/1985 | Johnson | 251/340 |
| 4,607,766 A | * | 8/1986 | Jones | 604/249 |
| 4,728,075 A | * | 3/1988 | Paradis | 251/340 |
| 5,228,647 A | * | 7/1993 | Ruibal Santome | 251/149.4 |
| 5,533,996 A | | 7/1996 | Murphey et al. | |
| 5,639,064 A | * | 6/1997 | deCler et al. | 251/149.5 |
| 5,738,144 A | | 4/1998 | Rogers | |
| 5,893,391 A | | 4/1999 | Jenski, Jr. | |
| 6,283,443 B1 | * | 9/2001 | Taneya | 251/149.6 |
| 6,543,745 B1 | | 4/2003 | Enerson | |
| 6,745,998 B1 | * | 6/2004 | Doyle | 251/149.6 |
| 2003/0032940 A1 | | 2/2003 | Doyle | |

FOREIGN PATENT DOCUMENTS

| | | |
|---|---|---|
| GB | 2118440 A | 11/1983 |
| WO | WO 03/013646 A2 | 2/2003 |

* cited by examiner

*Primary Examiner*—Eric Keasel
(74) *Attorney, Agent, or Firm*—Fulwider Patton LLP (57) ABSTRACT

A self-sealing male Luer connector for connection with a female Luer connector. The male Luer connector includes a housing having a distally-projecting tubular male body and a surrounding cuff interconnected by a proximal wall in which is formed at least one activation opening. A valve plug is slidably installed within the housing and formed with a distal end configured to sealingly engage the distal end of the male body's interior flow passage and with at least one activation arm at its proximal end configured to extend through the activation opening into the cavity formed between the male body and the cuff. An elastomeric device is sealingly configured within the activation opening about the activation arm to secure the valve plug in position and bias it distally. The proximal end of the male Luer connector may be configured as a conventional female connector, a blood collection device, or other such device.

15 Claims, 9 Drawing Sheets

SELF-SEALING MALE LUER CONNECTOR WITH BIASED VALVE PLUG

BACKGROUND

The present invention generally relates to medical connectors used in conducting fluids and more specifically to self-sealing male Luer connectors.

The self-sealing Luer connectors presently known and used in the art are generally designed to be connected to a patient's intravenous ("IV") or gas sampling line, drug or solution source, or other medical device such that the connector's seal operates to trap all fluid on the side of the connector toward the patient in the case of an IV line or other device such as a fluid bag in the case of a fluid source. In the case of some connectors, the connector has an unsealed male Luer connector on one end that remains connected to the patient's IV line, fluid source or other device and a self-sealing female connector on the opposite free end of the connector through which a syringe or other such device may be engaged. In the case of other connectors, the connector does not have a separate male connector end but is instead a permanent part of the line or source.

In use, the syringe or other device having a male connector is connected to the female end of the connector to push or pull fluids through the connector, as when medications are dispensed within a patient's IV line. The syringe or other device is configured with a male Luer connector so as to engage the self-sealing female connector and cause the male Luer's central boss to contact the female Luer's seal membrane, opening the slit formed in the membrane and creating a fluid path through the connector. After the necessary fluids have been dispensed or withdrawn, the syringe is removed and the slit in the needle-free connector's seal membrane closes to reseal the female connector and trap all bodily fluids, including any just-dispensed medications, on the patient side of the connector.

Therefore, the bodily fluids are sealed off within the self-sealing Luer connector toward the patient and away from the care giver, preventing any escape of the fluids and protecting both the patient and the care giver from possible dangerous contamination. However, the free end of the syringe and any residual fluids remaining therein are unsealed and exposed. Rather than the self-sealing, needle-free connectors known in the art remaining attached to the syringe to trap any and all residual fluids within the syringe, they remain on the destination or source connector to trap all residual fluids there instead.

While these prior art self-sealing, needle-free Luer connectors generally adequately serve their intended purpose of providing a sealed, needle-free connection that remains on a patient interface or the like and allows for the connection of a syringe or other such device to dispense or extract fluids, it is clear that these connectors are not designed to remain on and seal off the syringe itself before and after use and are not used for such a purpose. Moreover, while this function is not necessarily required in the typical drug dispensing application, there are other applications in which the fluid being dispensed from or drawn into the syringe must itself be at all times sealed off and exposure to such fluid by a care giver or patient prevented or at least minimized. For this purpose, a different self-sealing, needle-free Luer connector design is necessary.

Specifically, in the area of nuclear medicine where radioactive isotopes are administered to patients, it is critical that exposure to the isotopes be minimized for the safety of both the care giver and the patient. Yet, with the existing connectors known and used in the art, the isotope may be sealed off while still in its vial or other container prior to administration and may be sealed off on the patient side by the typical self-sealing, needle-free connector after administration, as discussed above, but the syringe or other device used to transfer the isotope from its container to the patient during administration is unsealed and allows exposure to the isotope.

Similarly, in collecting blood from a patient, the typical blood collection device known and used in the art has on one end an unsealed male Luer connector for attaching to the conventional female Luer connector on a patient's IV line. On the device's opposite end there is configured a needle having a resilient sleeve and surrounded by an elongate tubular shield. In use, the blood collection device's male Luer connector is connected to the IV line's female Luer connector, which starts the flow of blood through the connectors and into the needle. The sleeve covering the needle prevents the unwanted escape of any blood until a vacuum blood collection tube is inserted into the blood collection device's tubular shield. The collection tube is formed at its free end with a rubber stopper or septum that, upon insertion into the shield, pushes back the resilient sleeve covering the needle while the needle itself penetrates the septum and enters the tube, allowing the flow of blood through the blood collection device and into the vacuum collection tube. When the desired quantity of blood has been collected, the collection tube is removed from the device, allowing the resilient sleeve to expand back over the needle in covering relationship and to, again, prevent the further flow of blood from the patient through the connectors. As such, the blood collection device remains connected to the IV line and thereby seals off any residual blood remaining therein.

However, it is likely that at some point it will be desirable to remove the blood collection device from the IV line female connector, as when medicines are to be administered through the connector as discussed above. In this case, because the male Luer connector end of the conventional blood collection device is not self-sealing, the residual blood within the device will then be exposed to the care giver and others at the male Luer end when the device is disconnected. Moreover, there are other blood collection applications known in the art in which it is desirable to be able to leave the vacuum collection tube connected to the blood collection device, or even have the collection tube permanently mounted in the device, in which case, after the required quantity of blood has been collected, the male Luer connector end of the blood collection device must be disconnected from the female Luer connector of the patient's IV line. Again, with the typical blood collection device, this presents a hazard to the care giver, as the collection device's male Luer is unsealed and disconnection may expose the care giver to blood remaining within the device.

Yet a further example is in the oncology area where certain drugs have great beneficial effect when confined to the circulatory system of a patient, yet are harmful to the skin or other tissue of a patient. Such drugs must be carefully controlled so that they do not reach tissues that may be harmed. Transferring such drugs from one container to another or to the patient's fluid line can be hazardous if seals are not present.

Hence, those skilled in the art have recognized a need for a self-sealing male connector that may be connected to a syringe or other such device or formed on a blood collection device to seal off residual fluids therein before and after connection to a female connector. The present invention fulfills this need and others.

SUMMARY OF THE INVENTION

Briefly and in general terms, the present invention is directed to a connector comprising a male connector body having a proximal end and a distal end with a flow path opening at the distal end and an internal flow passage connected with the flow path opening, a valve element disposed within the male connector body in the internal flow passage and movable between a flow stop position at which the valve element seals the flow path opening against fluid flow and a flow position at which the valve element is removed from the flow path opening thereby allowing flow through the opening, and a valve element control device disposed external to the male connector body adjacent the proximal end of the male connector body and being movable towards the proximal end to control movement of the valve element to the flow position and being movable toward the distal end to control movement of the valve element to the flow stop position.

In more detailed aspects, the valve element seals the flow path opening from the internal flow passage inside the male connector body. The connector further comprises a base external to the male connector body and protruding outwards at the proximal end of the male connector body, the valve element control device extending through the base toward the distal end. The connector further comprises a biasing device disposed at the base so as to bias the valve element control device to control the valve element to the flow stop position. Further, the biasing device comprises a spring disposed so as to provide a biasing force to the valve element control device to control the valve element to move to the flow stop position. In more detail, the biasing device comprises an elastomeric material connected both to the base and to the valve element control device. The elastomeric material of the biasing device also seals the base where the valve element control device extends through the base against fluid flow through the base.

In other aspects, the connector further comprises a biasing device disposed so as to bias the valve element to the flow stop position. The connector further comprises a cuff located about the male connector body, the cuff having internal threads, whereby by means of the threads a female connector may be threaded into engagement with the male connector body and thereby held in engagement.

In yet further detailed aspects, the connector further comprises a second connector disposed at the proximal end of the of the male connector body, the second connector having a second connector internal flow passage connected with the male connector body internal flow passage such that fluid may flow between the male connector body and the second connector. The second connector comprises a female connector disposed at the proximal end of the of the male connector body, the female connector having a female connector internal flow passage connected with the male connector body internal flow passage such that fluid may flow between the male connector body and the female connector.

In more detail, the male connector body has an external male Luer tapered shape. The female connector has an internal female Luer tapered shape.

In yet other aspects, the invention is directed to a self-sealing male Luer connector for needle-free connection to the female Luer connector of a patient's IV line or other such medical device. The male Luer connector includes a housing having a central distally-projecting tubular male body and an outer cuff interconnected along a proximal housing wall so as to form a distally-opening cavity configured for receipt of the female Luer connector. The male body is formed with an internal bore or flow passage within which a valve plug is slidably installed. The valve plug is generally formed with a central lengthwise stem having a distal head configured to sealingly engage the distal end of the flow passage so as to selectively prevent fluid flow through the connector. At the opposite, proximal end of the valve plug, at least one upwardly-turned activation arm is configured so as to project distally into the cavity through an activation opening formed in the housing wall. An elastomeric sealing device is configured within the activation opening around the activation arm in order to hold the valve plug in place within the housing and bias the valve plug distally into sealing engagement with the male body's internal flow passage.

In a detailed aspect of the present invention, the internal flow passage through the tubular male body is formed with an annular inside surface that terminates distally in a proximally-facing nesting shoulder defining a central annular flow passage opening. The valve plug's distal head is formed with a distally-facing surface configured to engage the shoulder in surface-to-surface sealing contact.

In a more detailed aspect, the nesting shoulder is configured as a radially-inwardly-angled frusto-conical surface and the distally-facing surface of the head is configured as a corresponding frusto-conical surface.

In another more detailed aspect, the annular inside surface of the flow passage is distally-tapered. As such, the distal head of the valve plug is formed with a generally straight-walled side surface configured to provide clearance between the head and the flow passage inside surface when the valve plug is shifted proximally to unseat the distal head from the distal end of the flow passage.

In a related more detailed aspect, the annular inside surface of the flow passage is substantially straight-walled, and the distal head is formed with lengthwise, spaced-apart ribs to space the head from the flow passage's inside surface and provide a flow path therebetween.

In another detailed aspect of the present invention, the valve plug is formed at its proximal end with a base interconnecting the stem and the activation arm, the plug being configured such that the activation arm then protrudes distally through the activation opening substantially parallel to the stem when the plug is slidably received within the housing.

In a more detailed aspect, the valve plug stem is configured having a sufficient length to space the base from the proximal housing wall so as to provide for fluid flow through the flow passage around the base. Further, the stem's outside diameter is less than the annular inside surface of the flow passage so as to allow flow thereabout.

In another more detailed aspect, the male Luer connector is configured with two substantially opposite activation openings in the housing base and the valve plug is configured with two corresponding activation arms. In this way, the base formed at the proximal end of the valve plug is configured as an elongate bar positioned so as to extend symmetrically in opposite directions from the proximal end of the stem so as to form to opposite bar ends from which the respective activation arms project distally through the activation openings and into the cavity.

In yet another more detailed aspect, the valve plug may be formed as a single, unitary structure from a rigid thermoplastic material.

In a related more detailed aspect, the valve plug may be formed from a stem made of a rigid thermoplastic and a head made of a resilient material and configured to be mounted on the distal end of the stem.

In another detailed aspect of the male Luer connector of the present invention, the elastomeric device is an elastomeric sealing material bonded within the activation opening about the activation arm.

In a more detailed aspect, the elastomeric material is an ultraviolet cured acrylic.

In a further more detailed aspect, the activation opening in the housing's proximal wall is formed with a radially-inwardly projecting annular flange such that the elastomeric device encapsulates the flange when configured within the activation opening so as to anchor the device therein, thereby allowing the elastomeric device to sealingly and flexibly engage the activation arm and operably allow the activation arm to shift proximally with the proximal movement of a female Luer connector being inserted onto the male Luer connector of the present invention to, in turn, cause the valve plug to shift proximally to open the flow passage.

In another detailed aspect of the present invention, the housing cuff surrounding the male body is configured with internal threads to threadably engage the external thread portions formed on the female Luer connector so as to secure the connection and prevent inadvertent disengagement.

In another aspect of the present invention, a conventional female Luer connector is configured at the male Luer connector's proximal end so that the self-sealing male Luer connector may be mounted on a syringe in the typical fashion by threadably connecting the proximal female Luer connector to the distal end of the syringe. In another aspect, a blood collection device is formed on the proximal end of the male Luer connector so as to accommodate the typical vacuumized blood collection vial with pierceable septum. With the male Luer connector so configured, the distally-biased internal valve plug remains in its at-rest, distal position sealing off the flow passage and preventing the unwanted escape of any fluids from the connector and the device to which it is connected proximally. Then, when the distal male Luer connector is connected to the female Luer connector of the patient's IV interface, the valve plug's activation arm is engaged by the proximal end of the female Luer connector to shift the valve plug proximally, thereby unseating the valve plug from the distal end of the flow passage and allowing fluid flow through the connector.

In a more detailed aspect, the male body and the valve plug are configured such that the exterior cross-section of the male body sealingly engages the interior cross-section of the female Luer connector's tubular barrel as the barrel contacts the valve plug's activation arm to shift the valve plug proximally, thus causing the female Luer connector to be effectively sealingly connected to the male Luer connector before the flow passage is opened.

In a related more detailed aspect, if the female Luer connector is configured with a self-sealing internal piston, the male body and valve plug cooperate to activate the piston and allow flow through the female Luer connector after the male and female connectors have sealingly engaged along their respective tapered surfaces but before the valve plug is shifted proximally with further proximal movement of the female connector to open the flow passage through the male connector.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

Figure 1:
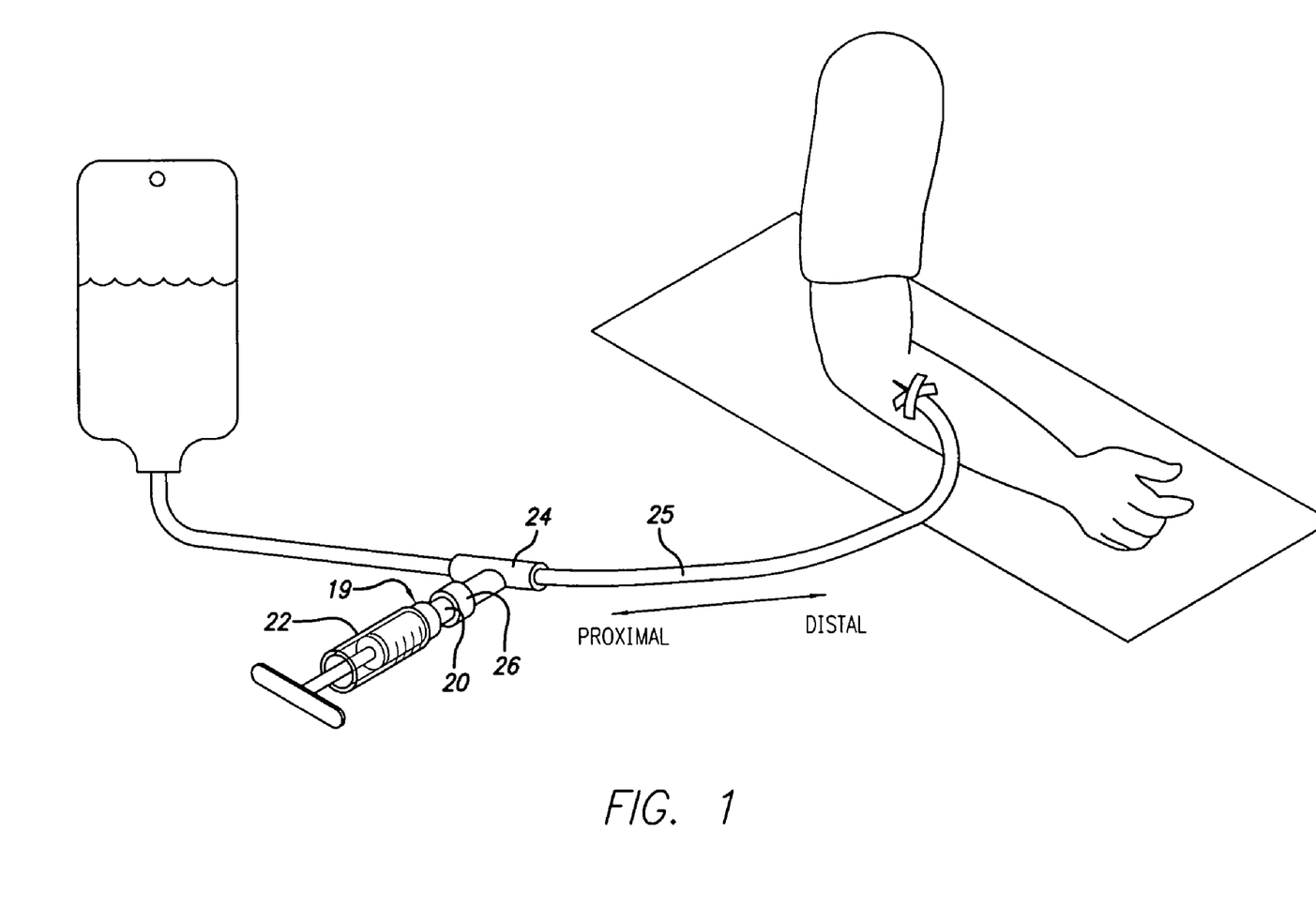
FIG. 1 is a simplified pictorial illustration of a patient IV interface operative in connection with an exemplary embodiment of the self-sealing male Luer connector in accordance with aspects of the present invention.

As shown in the drawings for purposes of illustration, wherein like reference numerals designate corresponding or like elements among the several views, and in the simplified pictorial illustration of FIG. 1, there is shown a connector 19 having a self-sealing male connector or fitting 20 mounted on the distal end of a syringe 22 and operably connected to the proximal end of a female connector 26 configured on a patient IV interface 24 for the administration or withdrawal of fluids through the IV line 25. It should be noted that here, and throughout, "distal" refers to the direction toward the patient and "proximal" refers to the direction away from the patient, or toward the syringe or other collection or dispensing device.

Figure 2:
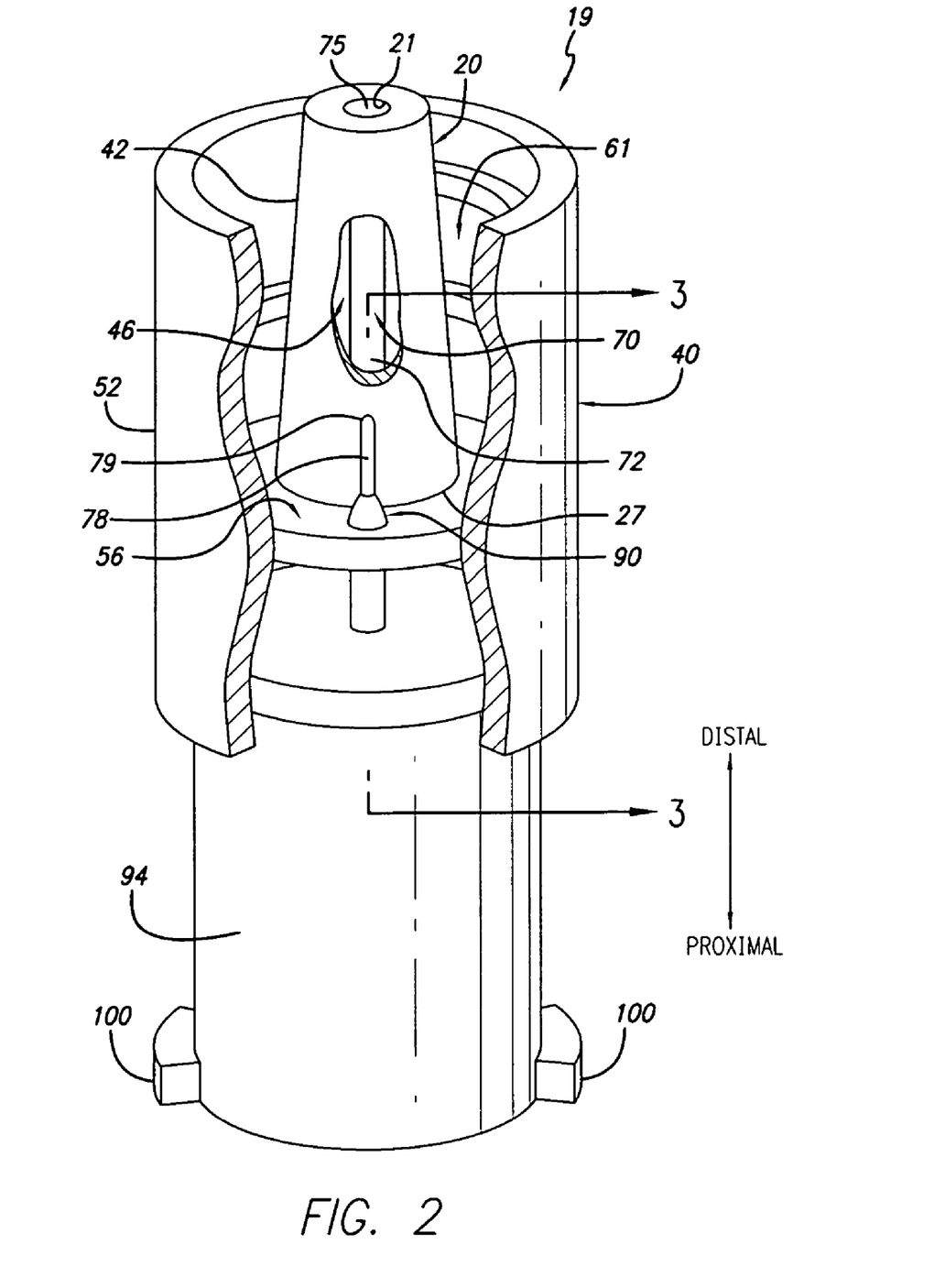
FIG. 2 is a perspective view, partially in section, of an exemplary embodiment of a self-sealing male Luer connector in accordance with aspects of the invention, including a housing having a male body disposed within a cuff, a valve plug, an elastomeric device, and a conventional female connector.

Referring to FIG. 2, there is shown a perspective view, partially in section, of an exemplary embodiment of the connector 19 of FIG. 1 having a self-sealing male connector 20 which in this case is a male Luer connector. The male Luer connector includes a housing 40 having a central distally-projecting tubular male body 42 and an outer cuff 52 interconnected with the male body by a base 56 at the proximal end 27 of the male body 42 so as to form a distally-opening cavity 61 configured for receiving a female Luer connector, such as the connector 26 shown in FIG. 3.

The male body is formed with an internal flow passage or bore 46 within which a valve element, which in this embodiment comprises a valve plug 70, is slidably installed. The valve plug is generally formed with a central lengthwise stem 72 having a distal head 75 configured to sealingly engage the distal end of the flow passage that forms a flow passage opening 21 located at the distal end of the male body so as to selectively prevent fluid flow through the connector. At the opposite, proximal end of the valve plug 70, at least one upwardly-turned activation arm 78 is configured so as to project distally into the cavity 61 through an activation opening 58 (shown in FIG. 3) formed in the base 56. An elastomeric sealing device 90 is configured within the activation opening around the activation arm in order to hold the valve plug in place within the housing and bias the valve plug distally into sealing engagement with the male body's internal flow passage.

In the case of the connector 19 embodiment of FIG. 2, a conventional female Luer connector 94 is formed at the proximal end 27 of the male body 42. The female Luer connector includes thread elements 100. It should be appreciated however that a variety of other connectors and devices, such as a shielded blood collection cannula device 95 (shown in FIG. 10), may be employed. As discussed more fully below, when the connector 19 having the self-sealing male Luer connector 20 of the present embodiment is mounted on a syringe 22 in the typical fashion by threadably connecting the proximal female Luer connector 94 to the male distal end of the syringe, so long as the distal male Luer connector is not connected to a female Luer connector, the valve plug 70 remains in its at-rest, flow stop, distal position at which it seals off the flow passage and prevents the unwanted escape of any fluids within the connector 19 and the syringe to which it is mounted (FIG. 1).

Referring further to FIG. 2, the activation arm 78 projecting distally from the proximal end of the valve plug 70 is shown as extending into the female Luer connector-receiving cavity 61 beyond the elastomeric sealing device 90 so that the distal end 79 of the arm is exposed. It will be appreciated that as a female Luer connector 26 (for example, that shown in FIG. 3) is inserted onto the male body 42 and advanced proximally (in the proximal direction), the proximal end of the female connector will come into contact with the distal end 79 of the arm. Then, further proximal movement of the female connector onto the male connector to fully seat will, in turn, proximally shift the valve plug through engagement of the activation arm with the female connector. As explained in detail below, proximal movement of the valve plug against the biasing force of the elastomeric device serves to unseat the valve plug's distal head from the distal end or flow passage opening 21 of the flow passage 46. Because, as shown, the valve plug stem 72 is narrow relative to the flow passage bore, once the male and female connectors are connected and the valve plug has shifted proximally to unseat the head and open the flow passage opening, fluid can flow around the stem and through the connectors. In this way, the self-sealing male Luer connector 20 closes and prevents flow therethrough when disconnected from a female connector, or the like, while it opens to a flow position and allows flow during connection. It will be appreciated by those skilled in the art that the male Luer connector is thus configured to be both self-sealing and to allow needleless connection to a female Luer connector, thereby protecting both the care giver and the patient from dangerous cross-contamination before, during and after use.

Figure 3:
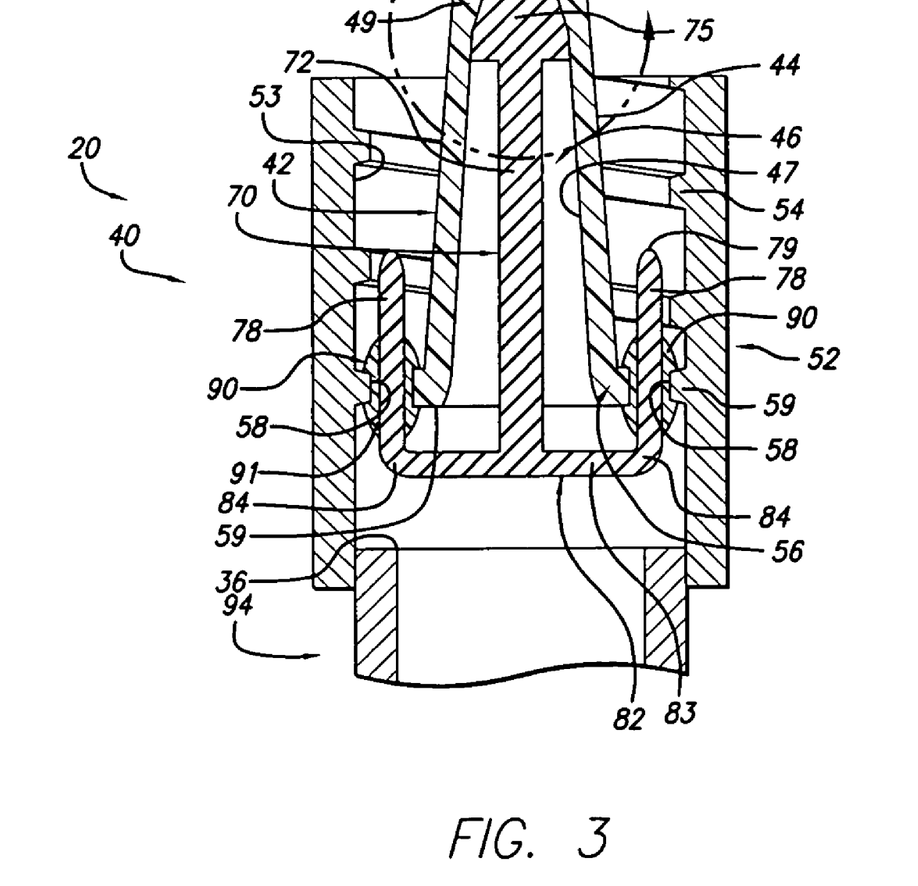
FIG. 3 is a partial cross-sectional view of the male Luer connector of FIG. 2 taken along line 3—3, also showing an adjacent self-sealing female Luer connector in section.

Referring now to FIG. 3, there is shown a partial cross-sectional view of the exemplary embodiment of the self-sealing male Luer connector 20 of the connector 19 of FIG. 2. As best shown in this view, the central lengthwise stem 72 of the valve plug 70 is positioned substantially coaxially within the flow passage 46 and terminates proximally in a linkage 82 defining a horizontal bar 83 on which are mounted one or more activation arms 78 at the respective opposite bar ends 84. Thus, the cross-section of the valve plug is generally an upside-down capital "T". The valve plug may then be formed with two substantially opposite activation arms configured to extend parallel to the stem from opposite ends of the linkage and to be aligned with and project distally through two corresponding activation holes 58 formed in the base 56. In this way, when a female Luer connector 26 is inserted onto the male Luer connector, as explained more fully below, the forces serving to shift the valve plug proximally are substantially symmetrical and balanced so as to obtain smooth, linear translation of the valve plug and, specifically, of each activation arm within its respective activation opening.

Each activation opening 58 may be defined by a radially-inwardly projecting annular flange 59 on which the elastomeric device 90 seats. In the exemplary embodiment, the flange is essentially formed by configuring the activation opening inside diameter to be smaller than the transverse dimension of the closed end of the distally-facing cavity 61 (FIG. 2) defined as the difference between the nominal inside diameter of the housing cuff 52 and the outside diameter of the proximal end of the male body 42. By providing such a flange about each activation opening, it will be appreciated that the elastomeric sealing device can be configured to completely encapsulate the flange as it seals around the activation arm so as to effectively anchor the device within the activation opening. In so doing, the elastomeric device serves to bond the valve plug 70 to the housing 40, to seal the activation openings in the housing wall about the activation arms, and to provide a biasing spring force to keep the valve plug seated distally within the flow passage. To achieve this function, the elastomeric device may consist of an elastomeric sealing material 91 such as Loctite® 3103 ultraviolet cured acrylic deposited within each activation opening while the respective activation arm is in position. Once cured, the elastomeric material has a high bond strength but allows substantial elongation so as to accommodate temporary proximal displacement of the valve plug during use of the male Luer connector. It also acts as a spring to bias the valve plug back to the flow stop position shown in FIG. 3.

With continued reference to FIG. 3, the flow passage 46 formed through the tubular male body 42 is shown in the exemplary embodiment male Luer connector 20 as having a distally-tapered annular inside surface 47 terminating distally in a radially-inward, proximally-facing nesting shoulder 49 so as to define a central flow passage opening 48 and act as a valve seat. As such, the distal head 75 of the valve plug 70 is configured to seat against the shoulder so as to achieve a surface-to-surface seal when the valve plug is forced into contact with the shoulder by a biasing device such as elastomeric device 90. As clearly shown in the view of FIG. 3, the valve plug's stem is configured with an outside diameter that is smaller than the nominal inside diameter of the flow passage so as to provide an annular space through which fluid can flow around the stem when the valve is opened. The stem is further formed having a sufficient length to space the valve plug's base 82 away from the proximally-facing surface of the housing wall 56 to provide clearance for the elastomeric device to fully seat about the annular flange 59 of the activation opening and to allow fluid flow around the base through the flow passage.

It will be appreciated by those skilled in the art that the configuration of the housing 40 shown in FIGS. 2 and 3 is well-suited for the injection molding manufacturing process, whereby the housing may be made in a relatively simple two-half mold cavity with a single core pull. Because the design of the housing is particularly suited to injection molding, then, it may be formed from a variety of plastic materials such as polyethylene, polypropylene, polycarbonate, PVC, ABS, acrylic and K-resin. Similarly, the valve plug 70 is also conveniently fabricated using a conventional injection molding process as is known and practiced in the art and thus may also be formed from a wide variety of plastics. As such, the male Luer connector is readily manufacturable with few moving parts. While a particular configuration of the housing and the valve plug having a pair of opposite respective activation openings 58 and arms 78 has been shown and described, it will be appreciated that various other configurations, such as an increased number of activation openings and arms spaced about the housing or various cross-sectional configurations for the openings and arms, may be employed without departing from the scope of the present invention.

Still referring to FIG. 3, the conventional female Luer connector 94 that is disposed at the proximal end of the male connector body and which extends proximally from the male Luer connector's housing 40 is shown in the exemplary embodiment as a separate component having its distal end press-fit within the housing's proximal end. It will be appreciated by those skilled in the art that the female Luer connector, like the housing and the valve plug 70, may be formed through an injection molding process and subsequently installed on the housing using a variety of assembly techniques now known or later developed in the art, including a press- or interference-fit, solvent bonding, or ultrasonic welding. As shown, the housing is of sufficient length proximal of the housing wall 56 such that the female Luer connector or other medical device can be installed proximally while leaving enough space between the distal end of the female Luer connector and the base 82 of the valve plug to allow the valve plug to translate proximally when the male Luer connector is connected to a patient's IV interface female connector 26 during use for example. Relatedly, it will be appreciated that the distal end 36 of the female Luer connector 94 may be configured to support a compression spring or the like which, when installed within the housing between the female Luer connector 94 and the base of the valve plug 82, may cooperate with the elastomeric device 90 to bias the valve plug distally so as to maintain a bias tending to maintain a seal between the valve plug head 75 and the flow passage distal shoulder 49.

The female Luer connector 26 of a patient's IV interface 24 (FIG. 1) shown adjacent the distal end of the male connector 20 is generally configured with a tubular barrel 28 having a distally-tapered interior surface 30 formed according to ANSI/AAMI/ISO standard 594.1 for medical connectors. The inner surface tapers inward in the distal direction from a larger diameter to a smaller diameter. A self-sealing piston 34 may be installed within the barrel having a selectively openable opening 35 responsive to compression of the piston upon insertion of a male Luer connector to open the opening and allow fluid flow through the female Luer connector. As will be discussed more fully below regarding FIGS. 4 and 5, the male body 42 of the self-sealing male Luer connector 20 is formed with a distally-tapered exterior surface 44 that tapers in the distal direction from a larger diameter to a smaller diameter, configured to sealingly engage the tapered inside surface of the female Luer connector when the two connectors are mated.

Figure 4:
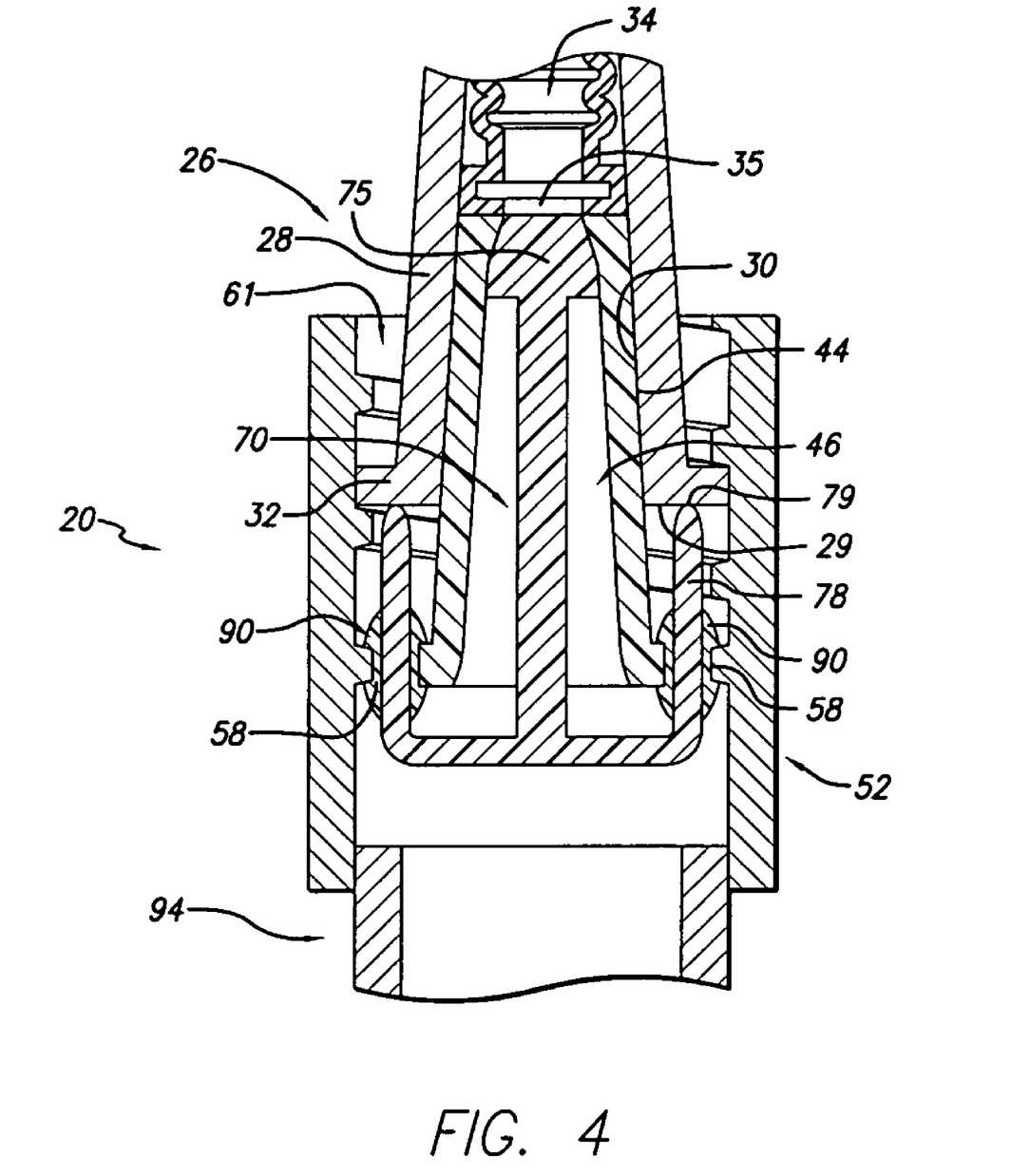
FIG. 4 is a partial cross-sectional view of the male Luer connector of FIG. 3 with the female Luer connector partially inserted thereon.

Turning, then, to FIG. 4, there is shown a partial cross-sectional view of the self-sealing male Luer connector 20 with the female Luer connector 26 partially inserted thereon. The valve element 75 of the connector 19 remains in the flow stop position. Specifically, the female Luer connector's tubular barrel 28 has been advanced proximally within the cavity 61 onto the male body 42 until the proximally-facing barrel abutment surface 29 has just come into contact with the distal ends 79 of the respective activation arms 78. In this position, the female Luer connector has not yet shifted the valve plug 70 proximally, so the distal head 75 remains in sealing engagement within the flow passage 46 due to the biasing force of the elastomeric device 90 mounted within the activation openings 58 about the valve plug's activation arms. However, the tubular male body has passed a sufficient distance within the female Luer connector's barrel to begin to form a taper-to-taper surface seal between the male body's outside surface 44 and the barrel's inside surface 30. Moreover, in this position, the passage of the distal end of the male body into the barrel has served to compress the self-sealing piston 34 and thereby open the opening 35. Therefore, it will be appreciated by those skilled in the art that the male Luer connector is so configured that upon partial connection with a self-sealing female Luer connector, the two connectors begin to seal along their corresponding distally-tapered surfaces and the self-sealing piston is activated before any fluid flow through the male Luer connector is allowed. Hence, the male Luer connector in accordance with the present invention provides for safe and effective needleless connection to a self-sealing female Luer connector with minimized risk of fluid escape by essentially causing the female Luer connector to be activated before the male Luer connector is activated through further proximal movement of the female Luer connector.

Figure 5:
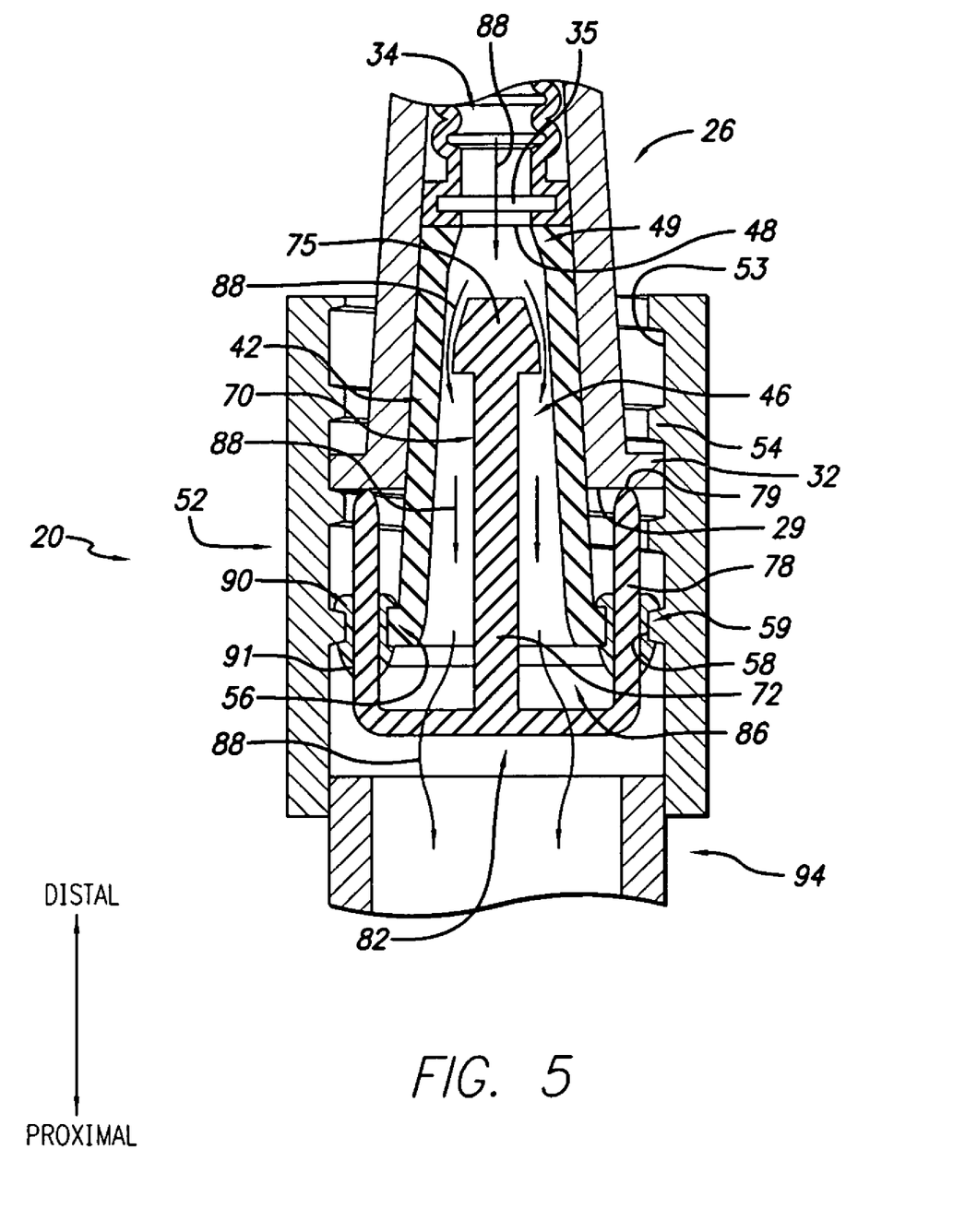
FIG. 5 is a partial cross-sectional view of the male Luer connector of FIG. 3 with the female Luer connector fully inserted thereon to activate the valve plug thereby permitting flow through the male connector.

Referring now to FIG. 5, there is shown a partial cross-sectional view of the female Luer connector 26 fully inserted onto the self-sealing male Luer connector 20. As such, through the engagement of the proximally-facing barrel abutment surface 29 with the distally-facing ends 79 of the activation arms 78, the valve plug 70 has shifted proximally with the further proximal movement of the female Luer connector against the biasing force of the elastomeric sealing device 90 to unseat the distal head 75 from the shoulder 49 and allow flow through the flow passage 46, thereby now activating the male Luer connector. The valve element is thus in the flow position. As shown, the elastomeric material 91 comprising the sealing device remains bonded to both the activation arms and the activation openings 58 as it stretches proximally with the proximal movement of the entire valve plug. It will be appreciated by those skilled in the art that while the bond strength of an ultraviolet cured acrylic or the like as the elastomeric material may alone be sufficient to resist the forces applied by the proximal movement of the female Luer connector, the radially-inward flanges 59 formed about each activation opening provide a seat on which the elastomeric device can anchor, thereby improving the device's strength and its ability to remain installed within the activation openings about the activation arms even under load.

With continued reference to FIG. 5, with both the female Luer connector 26's self-sealing piston 34 and the male Luer connector 20's valve plug 70 activated, a fluid flow path is now formed through both connectors. Thus, as shown by flow arrows 88, in an exemplary embodiment in which the male Luer connector is mounted on a syringe 22 (FIG. 1) and then connected to a patient's IV interface 24 (FIG. 1) so as to withdraw fluids, the fluid will flow through the female Luer connector's piston 34, its opening 35, the central flow passage opening 48 at the distal end of the flow passage 46, through the flow passage itself by passing around the distal head 75 and stem 72 of the valve plug, out the proximal end of the flow passage opening and through the flow openings 86 created by the space between the base 82 of the valve plug and the proximal housing wall 56, and through the proximal female Luer connector 94 into the syringe 22 (FIG. 1). The same flow path would be followed in reverse if medicines or other fluids are being dispensed from the syringe into the patient's IV line 25 (FIG. 1). In either case, once the desired quantity of fluids has been withdrawn into or dispensed from the syringe, the female Luer connector may then simply be disconnected from the male Luer connector, whereby the respective self-sealing devices would then reseal in the reverse order. That is, as the female Luer connector is withdrawn distally from the male Luer connector, the valve plug will reseal first under the biasing force exerted by the elastomeric device 90 when the female Luer connector reaches the position shown in FIG. 4. Further distal movement of the female Luer connector will completely disengage the proximally-facing barrel abutment surface 29 from the distal ends 79 of the activation arms 78 and will allow the self-sealing piston 34 to continue to expand until it reaches its at-rest position shown in FIG. 3 with the opening 35 again effectively closed. It will be appreciated that by having the valve plug reseal the male Luer connector before the taper-to-taper engagement between the outside and inside surfaces of the respective connectors is lost, any residual fluid in the syringe is effectively trapped on the syringe side by the valve plug, thereby preventing unwanted fluid escape and unnecessary risks of exposure and cross-contamination to the care giver and the patient. It will be further appreciated that the male Luer connector is easy to wipe and keep sanitary, as all engagement surfaces are exposed and easily accessible upon disconnection of the device from the female connector. The activation arms 78, and their linkage 82 and 83 thus form a valve element control device, with the arms disposed external to the male connector body adjacent the proximal end of the male connector body and being movable towards the proximal end, to control movement of the valve element to the flow position and being movable toward the distal end to control movement of the valve element to the flow stop position.

Referring to FIGS. 3–5, it can be seen that the female Luer connector 26 may be formed on the proximal end of its tubular barrel 28 with external thread elements or portions 32 as is known in the art. Accordingly, the inside surface 53 of the male Luer connector housing 40's cuff 52 may be formed with internal threads 54 configured to threadably engage the female Luer connector's external thread portions and thereby pull and secure the female connector in sealing engagement with the male connector. While it will be appreciated by those skilled in the art that the interference surface-to-surface fit between the respective distally-tapered surfaces of the male and female connectors may be sufficient to maintain connection between them during use, this means alone of securing the connection is not widely practiced, and the precautionary measure of the threadable engagement between the connectors as described and shown is preferred. It is to be understood, however, that numerous other connection means now known and later developed in the art for releasably securing male and female Luer connectors in sealing engagement may be employed without departing from the scope of the present invention.

Figure 6:
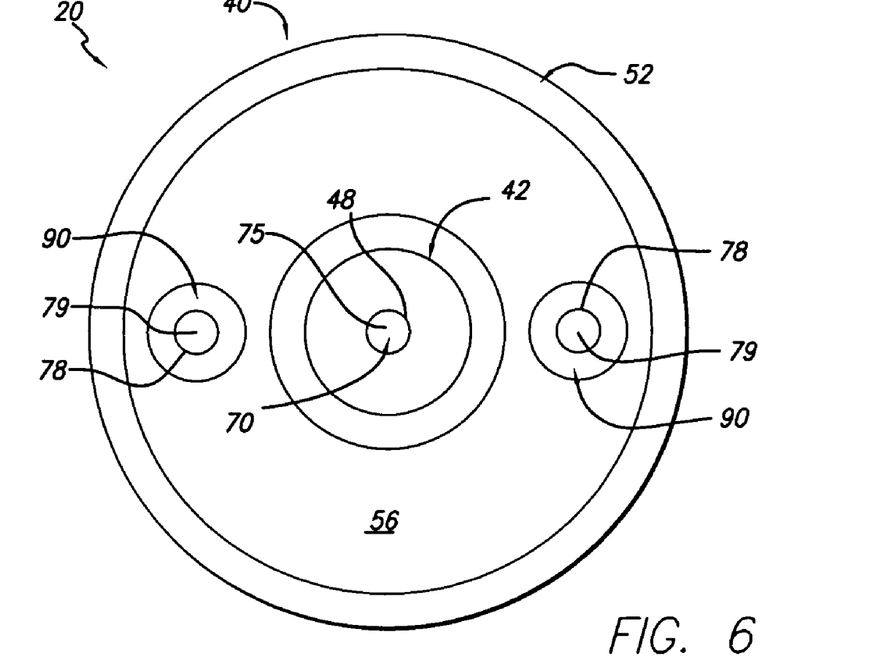
FIG. 6 is top view of the male Luer connector of FIG. 2.

Turning now to FIG. 6, there is seen a top view of the male Luer connector 20 of FIG. 2. As shown from the perspective, then, of essentially looking down into the distally-facing cavity 61 (FIG. 3) formed between the housing 40's outer cuff 52 and its inner distally-tapered tubular male body 42, there can be seen the orientation of the respective opposite activation arms 78 spaced about the male body and extending into the cavity from the housing's proximal wall 56. Again, the use of two activation arms essentially 180 degrees apart is only one of various arrangements possible in accordance with aspects of the present invention.

Figure 7:
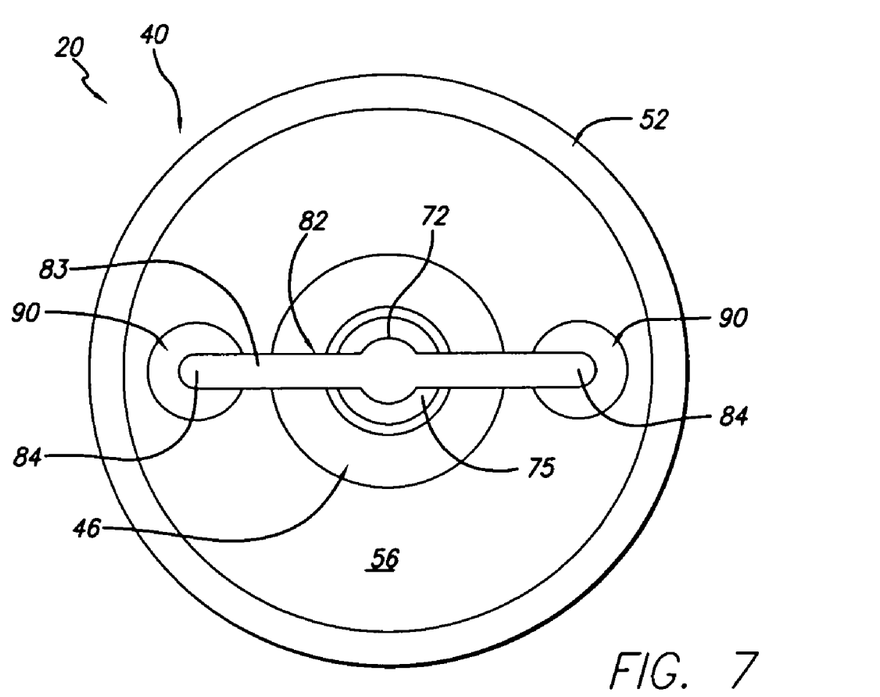
FIG. 7 is a bottom view of the male Luer connector of FIG. 2, with the conventional female Luer connector removed so that more details of the valve mechanism can be examined.

In FIG. 7 there is shown a bottom view of the male Luer connector of FIG. 2, with the proximally-projecting female Luer connector 94 (FIG. 2) removed for clarity in illustrating the relevant elements. As best seen in this view, the linkage 82 of the valve plug 70 (FIG. 3) is configured as a substantially linear bar 83 extending symmetrically in opposite directions away from the proximal end of the stem 72 so as to position the respective bar ends 84 substantially beneath the activation openings 58 (FIG. 3) so that the activation arms 78 (FIG. 3) extending distally away from the bar ends can freely translate within the activation openings. As also seen in this bottom view, the flow passage 46 is unhindered proximally by the base, allowing flow around the base with the valve plug in any position within the male body 42 (FIGS. 2–6), while the far, distal end of the flow passage is sealed off by the distal head 75 with the valve plug in the distally-biased position shown. It will be appreciated by those skilled in the art that during assembly of the valve plug within the housing, the plug will be inserted from the bottom as in FIG. 7 and then the activation arms will be bonded in place within the activation openings by inserting the elastomeric device 90 in and about the openings so as to essentially pot the valve plug in position within the valve with the distal head sealingly seated in the distal end of the flow passage. Again, though an elastomeric material has been shown and described as the means for sealingly securing the valve plug in place, it is to be understood that this variation is merely one embodiment. It will be appreciated by those skilled in the art that other devices for sealing moving parts that move relative to one another, such as gaskets, o-rings and the like, that are now known or later developed may be employed without departing from the scope of the present invention.

Referring now to FIGS. 8a–8e, there are shown enlarged partial cross-sectional views of various exemplary embodiments of the configuration of the distal end of the male body 42's flow passage 46 and the corresponding configuration of the valve plug 70's stem 72 and distal head 75 so as to selectively seal within the flow passage as discussed above. It is to be understood that these embodiments are exemplary only and that a variety of sealing arrangements are possible. First, with reference to FIG. 8a, there is seen the exemplary configuration of the male Luer connector 20 shown in FIGS. 2–7 wherein the flow passage has a distally-tapered interior surface 47 that terminates distally in a in a radially-inward, proximally-facing nesting shoulder 49. More specifically, as shown, the shoulder may be configured as a proximally-facing first frusto-conical surface 50. Accordingly, to provide for a surface-to-surface seal between the distal head and the shoulder, the distal head is configured with a distally-facing second frusto-conical surface 76 so as to correspond to the first frusto-conical surface. As also shown, the valve plug is formed as a unitary structure from a single material. As such, the stem and head may both be injection molded from a semirigid thermoplastic such that the stem has the necessary mechanical integrity to transmit the force exerted by the elastomeric device 90 (FIGS. 2 and 3) to the sealing surfaces of the distal head and flow passage so that they may engage to form a seal much like the tapered surfaces of the conventional male and female Luer connectors. Proximal of the second frusto-conical surface, the head transitions to a substantially straight-walled annular surface 77. It will be appreciated by those skilled in the art that as the valve plug is shifted proximally during use, as best seen in FIG. 5, these straight-wall surfaces provide for greater clearance between the head and the interior surface 47 of the flow passage, thereby improving the fluid flow around the head when the self-sealing male Luer connector is activated.

Figure 8:
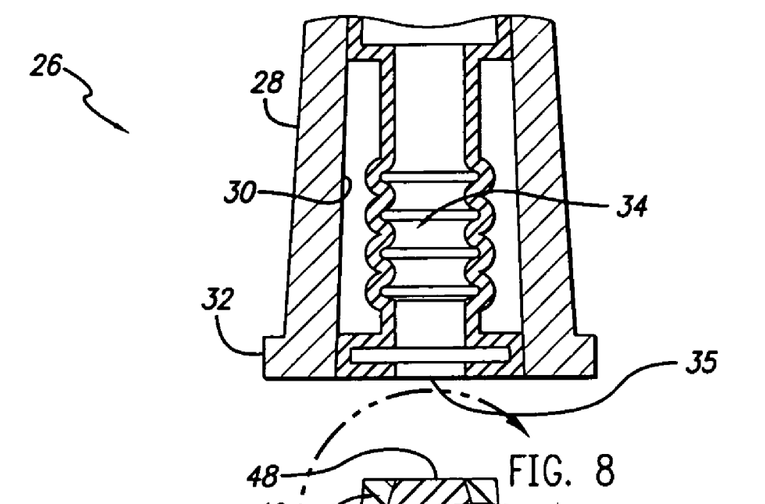
FIG. 8a is an enlarged partial cross-sectional view of the male Luer connector of FIG. 3 taken from circle 'FIG. 8' showing the distal configuration of the male body and the valve plug.
FIG. 8b is a partial cross-sectional view of an alternative embodiment of the distal configuration of the male body and the valve plug.
FIG. 8c is a partial cross-sectional view of an alternative embodiment of the distal configuration of the male body and the valve plug.
FIG. 8d is a partial cross-sectional view of an alternative embodiment of the distal configuration of the male body and the valve plug.
FIG. 8e is a partial cross-sectional view of an alternative embodiment of the distal configuration of the male body and the valve plug.
Figure 8A:
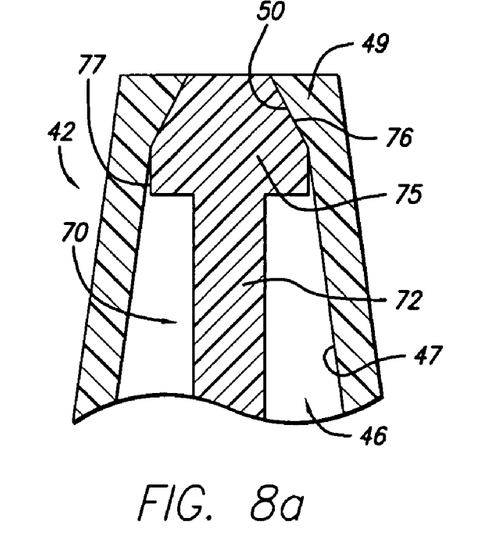
Figure 8B:
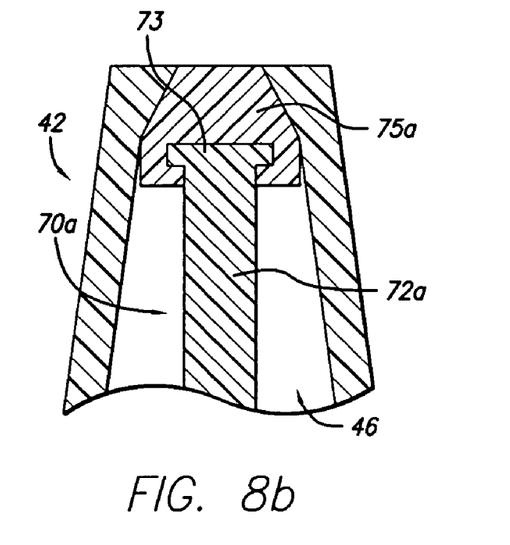

Turning to FIG. 8b, there is shown a male body 42 and valve plug 70a quite similar to that of FIG. 8a, with the exception that the stem 72a and head 75a are not formed of one material in a unitary construction. Rather, the stem is formed again of a rigid or semi-rigid material but is configured at its distal end with a distal flange 73. The head is then overmolded onto the distal end of the stem about the distal flange. In this way, it will be appreciated that the head may be made of a resilient, flexible material so as to seal within the distal end of the flow passage 46. For this purpose, the material of the head may be selected from a number of medical grade silicon rubbers, thermoplastic elastomers, and thermoplastic vulcanates. With the use of such a conforming material for the valve plug's distal head, it will be further appreciated that the head may be slightly oversized relative to the distal end of the flow passage so as to slightly compress the head when the valve plug is biased distally by the elastomeric sealing device 90 (FIGS. 2 and 3) and thereby insure a positive seal when the male Luer connector is disconnected or is otherwise not in use. Further, other than over-molding, it will be appreciated that a resilient head could be molded in a separate operation and mounted onto the valve stem using other assembly techniques now know or later developed in the art, such as solvent bonding or snap- or press-fit.

Figure 8C:
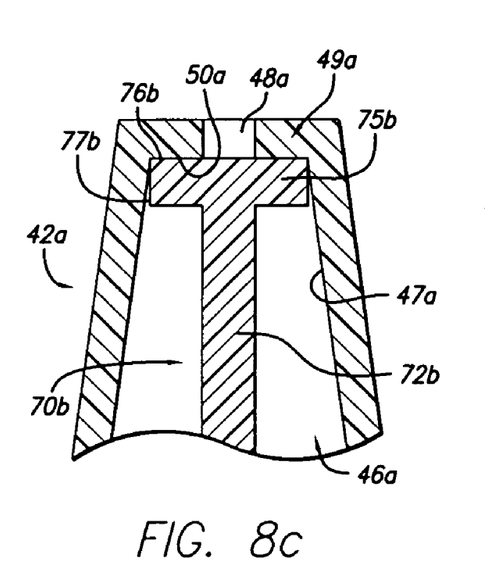
Figure 8D:
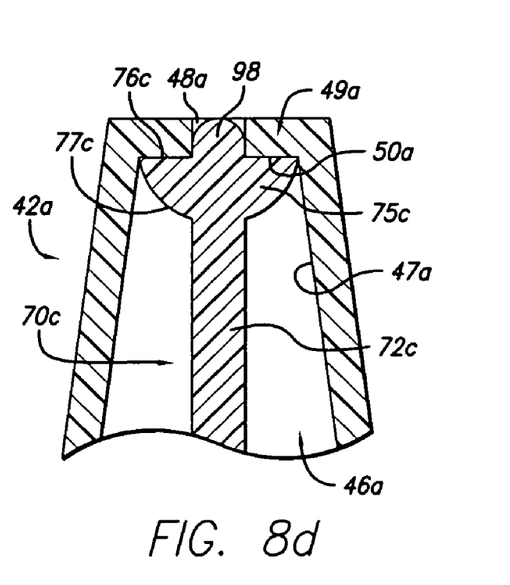

Turning now to FIGS. 8c and 8d, an alternative configuration for the radially-inwardly extending nesting shoulder 49a of the tubular male body 42a is shown wherein the shoulder is generally an annular flange that is perpendicular to the body's axis so as to form a squared proximally-facing sealing surface 50a. As previously, the annular flange defines a central flow passage opening 48a through which fluids can selectively pass from a female Luer connector 26 (FIG. 5) into the male Luer connector's flow passage 46a. In FIG. 8c, the valve plug 70b is shown as having a generally "T"-shaped cross-section formed by a vertical stem 72b and a horizontal distal head 75b. With the valve plug in its distally-biased position as shown, the distally-facing head sealing surface 76b is brought into surface-to-surface contact with the shoulder's proximally-facing sealing surface so as to create a face seal and prevent fluid flow through the connector. Then, when the valve as activated upon connection to a female Luer connector as described above and the distal head is shifted proximally, it will be appreciated that the straight-walled side surface 77b again allows fluid flow between the head and the distally-tapered interior surface 47a of the flow passage.

Similarly, as shown in the alternative exemplary embodiment of FIG. 8d, the distal head 75c may be configured with a substantially planar, distally-facing sealing surface 76c configured to create a face seal against the nesting shoulder 49a's proximally-facing sealing surface 50a when the valve plug 70c is biased distally within the flow passage 46a. In addition, a distally-projecting head plug 98 may be configured on the head's distally-facing surface so as to effectively plug and seal within the central flow passage opening 48a. In this way, more surface-to-surface engagement is provided to further effectuate a positive seal between the valve plug head and the distal end of the flow passage. The distal end of the head plug may be rounded to facilitate centering and seating the head plug within the flow passage opening. As also shown in FIG. 8d, the side surface 77c of the head may be proximally-tapered or radiused inwardly to provide further clearance between the head and the interior surface 47a of the flow passage when the valve is activated.

Figure 8E:
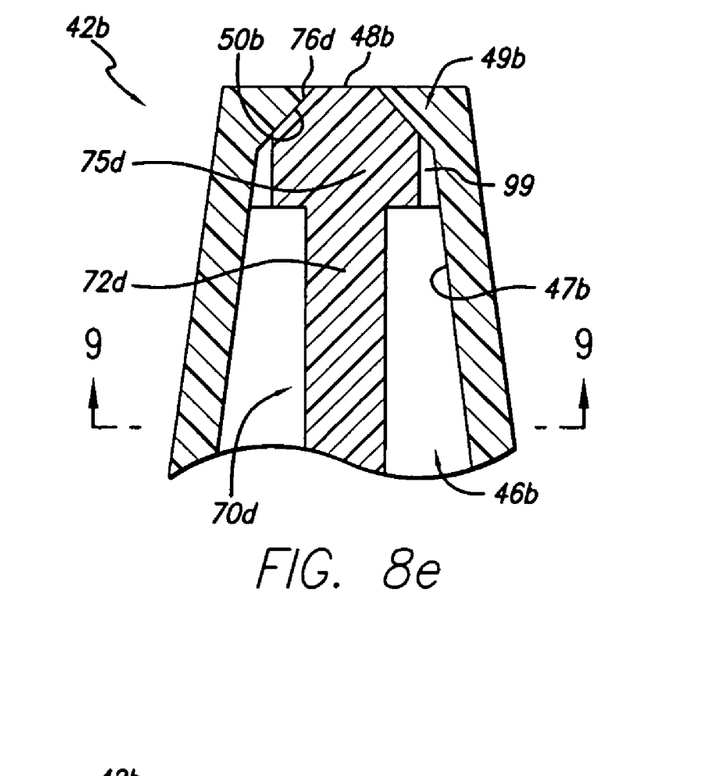

In FIG. 8e there is shown an alternative configuration of the tubular male body 42b in which the flow passage 46b is formed having a substantially straight-walled interior surface 47b parallel with the flow passage's central axis. The flow passage again terminates distally in a radially-inwardly-projecting, distally-tapered nesting shoulder 49b defining a central flow passage opening 48b and a proximally-facing first frusto-conical surface 50b. Due to the non-tapered interior surface of the flow passage, it will be appreciated by those skilled in the art that the previous exemplary valve plug and head configurations will not effectively open the flow passage when the valve plug is shifted proximally upon connection to a female Luer connector 26 (FIG. 5). As such, the distal head 75d of the exemplary embodiment of FIG. 8e is configured with a central solid portion having lengthwise ribs 99 spaced thereabout to allow for fluid communication around the head once the distal end of the head has unseated from the distal end of the flow passage. Specifically, the central portion of the head is formed distally with a distally-facing second frusto-conical surface configured to sealingly engage the shoulder's first frusto-conical surface when the valve plug is biased distally within the flow passage, much like the sealing engagement of the exemplary embodiments of FIGS. 8a and 8b. Then, when the valve plug is shifted proximally during connection with a female Luer connector, the first and second frusto-conical surfaces are disengaged to allow flow through the central flow passage opening into the flow passage.

Figure 9:
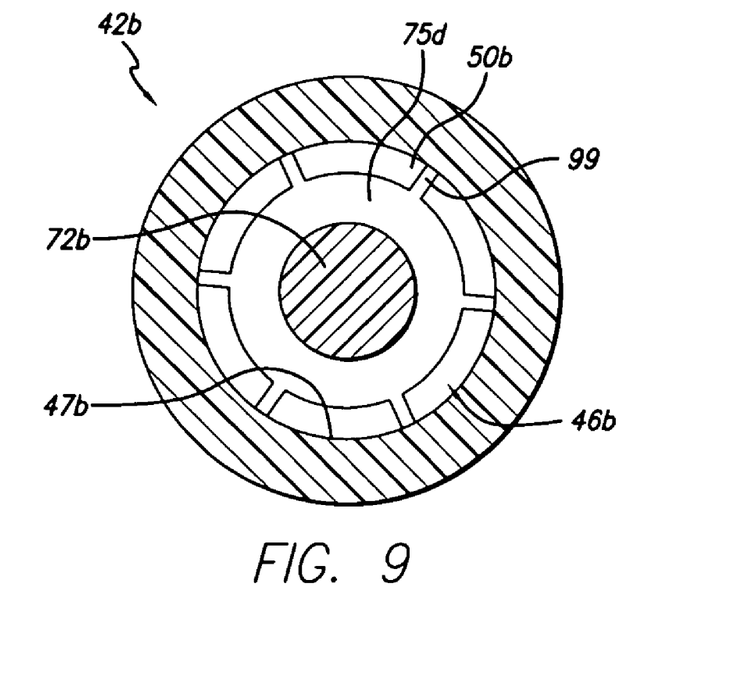
FIG. 9 is a cross-sectional view of the alternative embodiment of the distal configuration of the male body and the valve plug shown in FIG. 8e taken along line 9—9.

As best seen in FIG. 9, fluid flow can continue through the flow passage 46b around the valve plug's distal head 75d by passing about the head's solid portion between the circumferentially spaced-apart ribs 99 and then around the narrower stem 72d and on through the connector as described previously. Thus, the ribs serve as spacers to space the solid central portion of the distal head away from the interior surface 47b of the flow passage, thereby allowing fluid flow around the head. The ribs further serve to keep the stem and head centered within the flow passage as the valve plug 70d translates axially therein during use of the male Luer connector. It is noted that the taper-to-taper engagement between the distal head and the shoulder 49b (FIG. 8e) can alone serve to center the head as it seats in the distal end of the flow passage so as to effectively close the flow passage opening and that this function in combination with the stiffness of the stem may allow for the activation of the valve within a straight-walled flow passage without the use of the ribbed spacers. Hence, it will be appreciated that various other valve plug configurations with or without the ribbed spacers may be employed without departing from the scope of the invention.

Furthermore, it will again be appreciated by those skilled in the art that the exemplary distal head and flow passage configurations shown and described in FIGS. 8a–8e are merely illustrative of selectively sealable arrangements for the respective engaging components that are possible and are in no way limiting of the scope of the present invention. By way of example, just as with the embodiment of FIG. 8a as illustrated in FIG. 8b, it will be appreciated that the exemplary embodiment male Luer connectors of FIGS. 8c–8e may also be configured with the valve plug having a single, unitary construction or with the stem of a rigid or semi-rigid plastic and a resilient head overmolded or otherwise mounted onto the stem's distal end.

Figure 10:
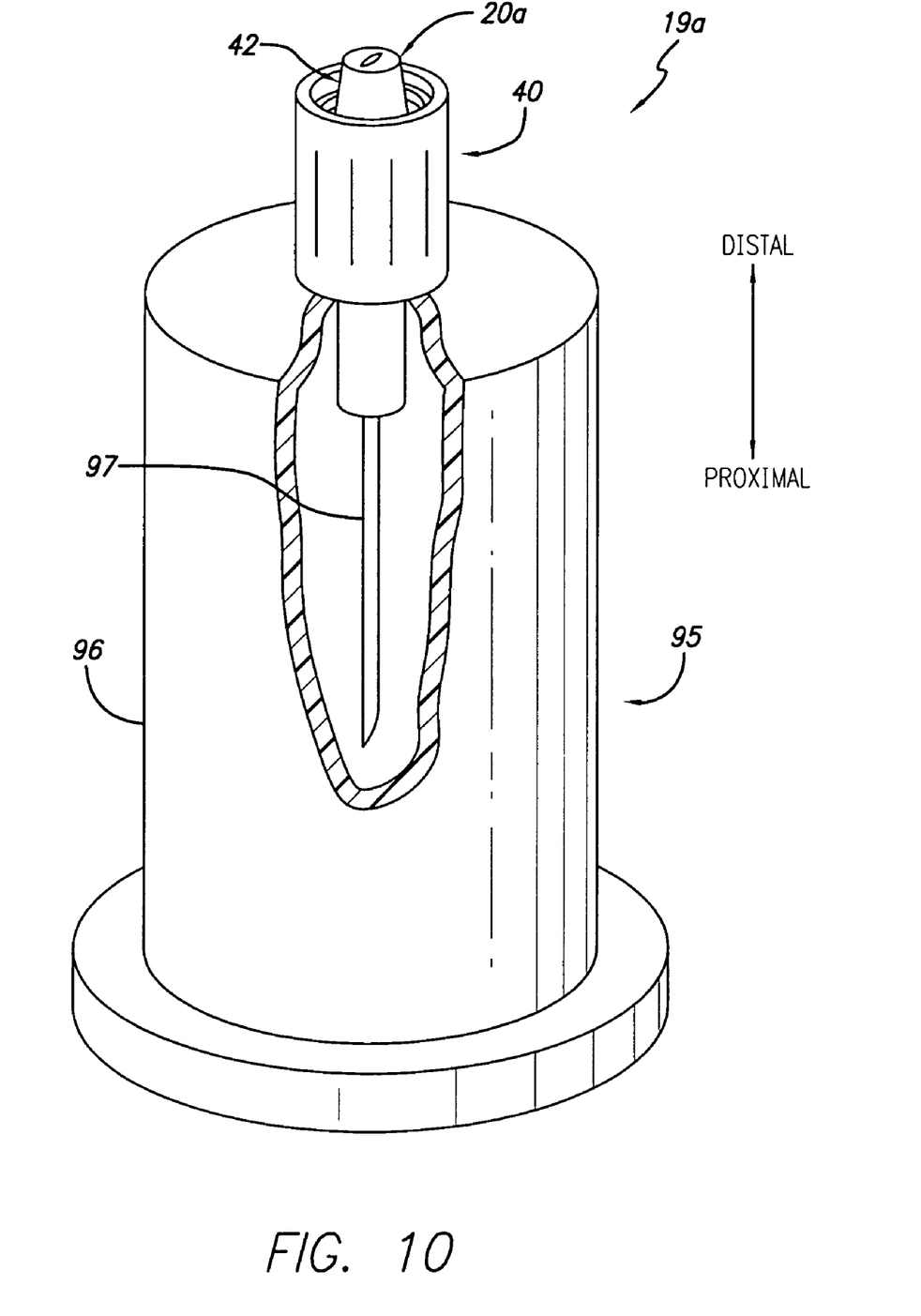
FIG. 10 is a perspective view, partially in section, of an alternative embodiment self-sealing male Luer connector, including a housing having a male body disposed within a cuff and a blood collection device.

Referring now to FIG. 10, there is shown an alternative embodiment of a connector 19a having a male Luer connector 20a having a blood collection device 95 mounted opposite the housing 40. The blood collection device, which is known and used in the art, includes a proximally-extending needle cannula 97 and a shield 96 mounted about the needle so as to protect care givers and patients from accidental needle punctures. So configured, the connector's male body 42 may be connected to the female Luer connector 26 of a patient's IV interface 24 (FIG. 1), as discussed above, to activate the internal valve plug 70 (FIG. 2) and create a needle-free flow path between the patient's IV line 25 (FIG. 1) and the needle through the male Luer connector. As is known in the art, a resilient boot (not shown) over the needle prevents the flow of fluid through the needle until a vacuumized blood collection vial with septum (not shown) is inserted within the blood collection device shield to push the boot up the needle while the needle then penetrates the septum to allow fluid to flow therethrough into the vial. When the vial is full, it may be removed from the blood collection device and another installed therein until the desired quantity of blood has been withdrawn. Then, the male connector may simply be disconnected from the female connector on the patient's IV line and discarded. From the foregoing, it will be appreciated that upon disconnection, the valve plug is shifted proximally by the elastomeric device 90 (FIG. 2) installed within the housing, thereby causing the distal head 75 (FIG. 3) to reseal within the flow passage 46 (FIG. 3) to trap all blood and other fluids within the male Luer connector for safe disposal. Thus, in this embodiment, as with the exemplary embodiment including a conventional female connector, the self-sealing internal valve plug operably installed within the male connector serves to safely and easily connect to and disconnect from the female Luer connector of a patient's IV line for the effective and controlled administration and/or withdrawal of fluids.

Therefore, the male Luer connector is well-suited for connection to a syringe or other device used to transfer fluids to and from a patient without compromising the patient's or the care giver's safety. While particular forms of the invention have been illustrated and described, it will also be apparent to those skilled in the art that various modifications can be made without departing from the spirit and scope of the invention. Accordingly, it is not intended that the invention be limited except by the appended claims.

What is claimed is:

1. A connector comprising:
   a male connector body having a proximal end and a distal end with a flow passage opening at the distal end and an internal flow passage connected with the flow passage opening;
   a valve element disposed within the male connector body in the internal flow passage and having a valve element head movable between a flow stop position at which the valve element head engages the distal end from within the flow passage and seals the flow passage opening against fluid flow and a flow position at which the valve element head is moved in a proximal direction away from the flow passage opening thereby allowing flow through the opening;
   a valve element control device disposed external to the male connector body adjacent the proximal end of the male connector body and being movable towards the proximal end to control movement of the valve element head in a proximal direction to the flow position and being movable toward the distal end to control movement of the valve element head in a distal direction to the flow stop position; and
   a biasing device connected to the valve element control device and configured to urge the valve element head to move in a distal direction to the flow stop position when a force applied in a proximal direction to the valve element control device is removed.

2. The connector of claim 1 wherein the valve element seals the flow passage opening from the internal flow passage inside the male connector body.

3. The connector of claim 1 further comprising a base external to the male connector body and protruding outwards at the proximal end of the male connector body, the valve element control device extending through the base toward the distal end.

4. The connector of claim 3 further comprising a biasing device disposed at the base so as to bias the valve element control device to control the valve element to the flow stop position.

5. The connector of claim 4 wherein the biasing device comprises an elastomeric material connected both to the base and to the valve element control device.

6. The connector of claim 5 wherein the elastomeric material of the biasing device also seals the base where the valve element control device extends through the base against fluid flow through the base.

7. The connector of claim 1 further comprising a cuff located about the male connector body, the cuff having internal threads, whereby by means of the threads a female connector may be threaded into engagement with the male connector body and thereby held in engagement.

8. The connector of claim 1 further comprising a second connector disposed at the proximal end of the male connector body, the second connector having a second connector internal flow passage connected with the male connector body internal flow passage such that fluid may flow between the male connector body and the second connector.

9. The connector of claim 8 wherein the second connector includes a female connector.

10. The connector of claim 9 wherein the male connector body has an external male Luer tapered shape.

11. The connector of claim 10 wherein the female connector has an internal female Luer tapered shape.

12. The connector of claim 1 wherein the male connector body has an external male Luer tapered shape.

13. A connector comprising:

a male connector body having a proximal end and a distal end with a flow passage opening at the distal end and an internal flow passage connected with the flow passage opening;

a valve element disposed within the male connector body in the internal flow passage and movable between a flow stop position at which the valve element seals the flow passage opening against fluid flow and a flow position at which the valve element is removed from the flow passage opening thereby allowing flow through the opening;

a valve element control device disposed external to the male connector body adjacent the proximal end of the male connector body and being movable towards the proximal end to control movement of the valve element to the flow position and being movable toward the distal end to control movement of the valve element to the flow stop position; and a resilient biasing device connected to the valve element control device and configured to urge the valve element to move in a distal direction to the flow stop position when a force applied in a proximal direction to the valve element control device has been removed.

14. A connector comprising:

a male connector body having a proximal end and a distal end with a flow passage opening at the distal end and an internal flow passage connected with the flow passage opening;

a valve element disposed within the male connector body in the internal flow passage and movable between a flow stop position at which the valve element engages the distal end and seals the flow passage opening against fluid flow and a flow position at which the valve element is removed from the flow passage opening thereby allowing flow through the opening;

a valve element control device disposed external to the male connector body adjacent the proximal end of the male connector body and being movable towards the proximal end to control movement of the valve element to the flow position and being movable toward the distal end to control movement of the valve element to the flow stop position;

a base external to the male connector body and protruding outwards at the proximal end of the male connector body, the valve element control device extending through the base toward the distal end; and a biasing device disposed at the base so as to bias the valve element control device to control the valve element to the flow stop position, the biasing device comprising an elastomeric material connected both to the base and to the valve element control device.

15. The connector of claim 14 wherein the elastomeric material of the biasing device also seals the base where the valve element control device extends through the base against fluid flow through the base.

* * * * *